United States Patent
Pyles

(10) Patent No.: US 11,957,907 B2
(45) Date of Patent: Apr. 16, 2024

(54) TREATING LUNG DISEASE WITH SPINAL CORD STIMULATION

(71) Applicant: Spiro Medical, Inc., Belleair Bluffs, FL (US)

(72) Inventor: Stephen T. Pyles, Ocala, FL (US)

(73) Assignee: Spiro Medical, Inc., Belleair Bluffs, FL (US)

( * ) Notice: Subject to any disclaimer, the term of this patent is extended or adjusted under 35 U.S.C. 154(b) by 0 days.

(21) Appl. No.: 17/657,136

(22) Filed: Mar. 30, 2022

(65) Prior Publication Data

US 2022/0313991 A1    Oct. 6, 2022

Related U.S. Application Data

(60) Provisional application No. 63/240,155, filed on Sep. 2, 2021, provisional application No. 63/168,702, filed on Mar. 31, 2021.

(51) Int. Cl.
*A61N 1/36*     (2006.01)
*A61N 1/05*     (2006.01)

(52) U.S. Cl.
CPC ......... *A61N 1/3601* (2013.01); *A61N 1/0551* (2013.01); *A61N 1/36062* (2017.08); *A61N 1/36071* (2013.01); *A61N 1/36171* (2013.01); *A61N 1/36175* (2013.01)

(58) Field of Classification Search
CPC ............... A61N 1/3601; A61N 1/0551; A61N 1/36062; A61N 1/36071; A61N 1/36171; A61N 1/36175
See application file for complete search history.

(56) References Cited

U.S. PATENT DOCUMENTS

| | | | |
|---|---|---|---|
| 9,656,080 B2 | 5/2017 | Chiu et al. | |
| 2008/0051851 A1 | 2/2008 | Lin | |
| 2010/0174340 A1* | 7/2010 | Simon | A61N 1/0551 607/116 |
| 2010/0179562 A1* | 7/2010 | Linker | A61N 1/0551 607/117 |
| 2010/0198308 A1* | 8/2010 | Zhou | A61N 1/36521 607/62 |
| 2011/0184486 A1* | 7/2011 | De Ridder | A61N 1/0529 607/45 |
| 2012/0277839 A1* | 11/2012 | Kramer | A61N 1/36057 607/118 |
| 2013/0204334 A1 | 8/2013 | Simon et al. | |
| 2016/0144180 A1 | 5/2016 | Simon et al. | |
| 2016/0263376 A1* | 9/2016 | Yoo | A61N 1/36017 |

(Continued)

OTHER PUBLICATIONS

PCT International Search Report for PCT/US2022/022608 dated Jul. 22, 2022 (5 pages).

(Continued)

*Primary Examiner* — Eugene T Wu
(74) *Attorney, Agent, or Firm* — Merchant & Gould P.C.

(57) ABSTRACT

A kit for treating lung disease includes at least one lead having at least one contact, and a pulse generator configured to connect to the least one lead. The pulse generator is programmed to generate electrical signals for transmission through the at least one lead and for release by the at least one contact in a predetermined location of an epidural space to mitigate lung disease symptoms.

5 Claims, 5 Drawing Sheets

(56) References Cited

U.S. PATENT DOCUMENTS

2017/0021161 A1 1/2017 De Ridder
2017/0312499 A1 11/2017 Linker et al.

OTHER PUBLICATIONS

Staats et al., "The Use of Non-invasive Vagus Nerve Stimulation to Treat Respiratory Symptoms Associated with Covid-19: A Theoretical Hypothesis and Early Clinical Experience", Neuromodulation: Technology at the Neural Interface, Wiley Periodicals LLC, Aug. 2020, 2 pages.

* cited by examiner

TREATING LUNG DISEASE WITH SPINAL CORD STIMULATION

CROSS-REFERENCE TO RELATED APPLICATIONS

This application claims the benefit of and priority to U.S. Provisional Patent Application No. 63/168,702, filed Mar. 31, 2021, and U.S. Provisional Patent Application No. 63/240,155, filed Sep. 2, 2021, the disclosures of which are herein incorporated by reference in their entireties.

BACKGROUND

Asthma is a long-term inflammatory disease of the airways of the lungs. There are about three million new asthma diagnoses annually in the United States. Although there is treatment that can help manage asthma, there is no known cure.

Asthma can severely effect ones quality of life by making it difficult to breathe. Asthma symptoms include shortness of breath, difficulty breathing, wheezing, coughing, and tightness of the chest. It is not uncommon for asthma patients to have frequent emergency room visits which often result in a hospital admission.

Asthma attacks are sudden worsening of asthma symptoms caused by tightening of muscles around the bronchioles. Asthma attacks can cause respiratory failure, unconsciousness, and even death. Asthma attacks can be caused by changes in air temperature, dust, dander, smoke, pollen, and chemical fumes. In some instances, emotional stress, exercise, and gastric reflux can cause an asthma attack. Additionally, certain medications like beta blockers, non-steroidal anti-inflammatory drugs (NSAIDs), and aspirin can lead to an asthma attack.

Oral medications, inhalers, and injections are commonly used treatments for the relief of bronchospasm associated with asthma. More recently, immunosuppressants known as "biologic" medications have been used. However, none of these treatments can provide consistent relief, and side effects from these medications are common.

SUMMARY

In general terms, the present disclosure relates to treating lung diseases such as asthma and/or chronic obstructive pulmonary disease (COPD) with spinal cord stimulation. Various aspects are described in this disclosure, which include, but are not limited to, the following aspects.

In one aspect, a kit for treating lung disease comprises at least one lead having at least one contact; and a pulse generator configured to connect to the at least one lead, and the pulse generator being programmed to generate electrical signals for transmission through the at least one lead and for release by the at least one contact in a predetermined location of an epidural space to mitigate lung disease symptoms.

In another aspect, a method of treating lung disease comprises implanting at least one lead to have at least one contact positioned in a predetermined location of an epidural space; connecting the at least one lead to a pulse generator; and programming the pulse generator to generate electrical signals for release by the at least one contact in the predetermined location to mitigate lung disease symptoms.

DESCRIPTION OF THE FIGURES

The following drawing figures, which form a part of this application, are illustrative of the described technology and are not meant to limit the scope of the disclosure in any manner.

DETAILED DESCRIPTION

Figure 1:
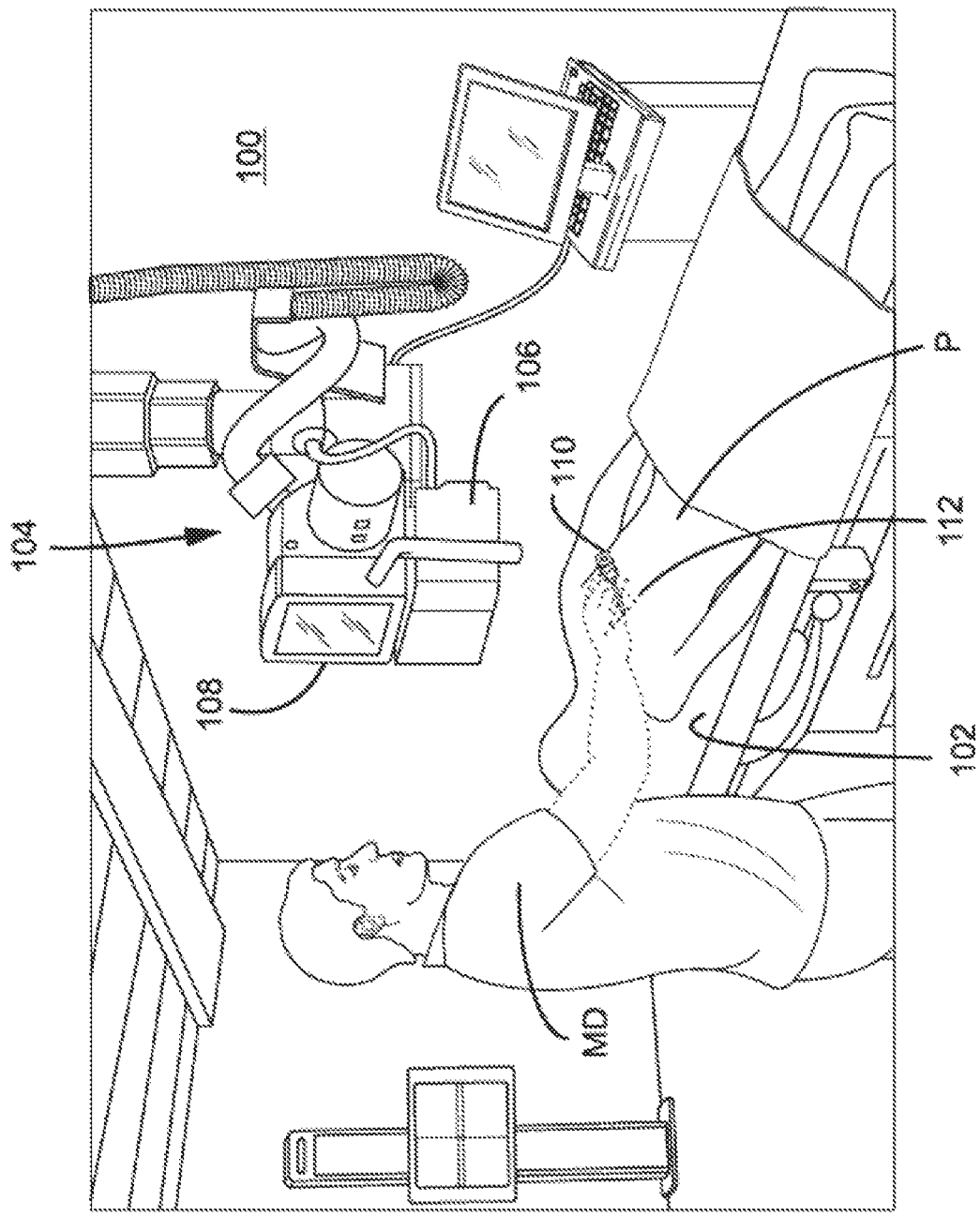
FIG. 1 illustrates an example of a system for performing a procedure to implant one or more leads for spinal cord stimulation.

FIG. 1 illustrates an example of a system 100 for performing a procedure to implant one or more leads for spinal cord stimulation. In some examples, an epidural needle 110 is used to implant temporary percutaneous leads for a trial spinal cord stimulation procedure. In alternative examples, the epidural needle 110 is used to implant permanent percutaneous leads. The system 100 includes a table 102 on which a patient P rests face down. The patient P's back is exposed for a physician MD to insert the epidural needle 110.

The epidural needle 110 is inserted into the skin, and through the paravertebral muscles until it reaches the lamina next to the spinous process located just below a selected target location in the epidural space of the patient P's spine. The epidural needle 110 is then advanced through the ligamentum flavum and into the epidural space. The epidural space is located between the dura mater and the wall of the spinal canal. The epidural space contains fat, veins, arteries, spinal nerve roots and lymphatics. As will be described in more detail below, a distal end of at least one lead having at least one contact is implanted in the epidural space to release electrical signals for treating asthma by spinal cord stimulation. In addition to treating asthma, the electrical signals released by the at least one contact can also mitigate pain.

The system 100 includes a fluoroscopy system 104 that has at least an imaging device 106 that captures fluoroscopy images (i.e., X-ray images) of the patient P's spine, and a display device 108 that displays the fluoroscopy images for viewing by the physician MD. The physician MD can view the fluoroscopy images for guidance when inserting the epidural needle 110 in the patient P's epidural space, and while implanting the leads into the patient P's epidural space.

As an illustrative example, the physician MD inserts the epidural needle 110 into the epidural space of the patient P's spine, and thereafter threads one or more insulated wire leads through the epidural needle 110 to implant the distal ends of the leads into the epidural space. As an example, the distal end of at least one lead is implanted into the posterior epidural space between the thoracic vertebrae T1-T5 (see FIG. 3) to ensure that the leads are effective in providing desired treatment. The epidural space between thoracic vertebrae T1-T5 is a location where the electrical signals released by the at least one contact are effective for treating asthma.

In the example shown in FIG. 1, a pattern of markings 112 are drawn on the patient P's back. The pattern of markings 112 can be used by the physician MD as a path for guiding the insertion of the epidural needle 110 into the patient P's spine at a correct angle. The pattern of markings 112 can be drawn by using a device described in U.S. patent application Ser. No. 17/113,232, filed Dec. 7, 2020, the entirety of which is hereby incorporated by reference.

Figure 2:
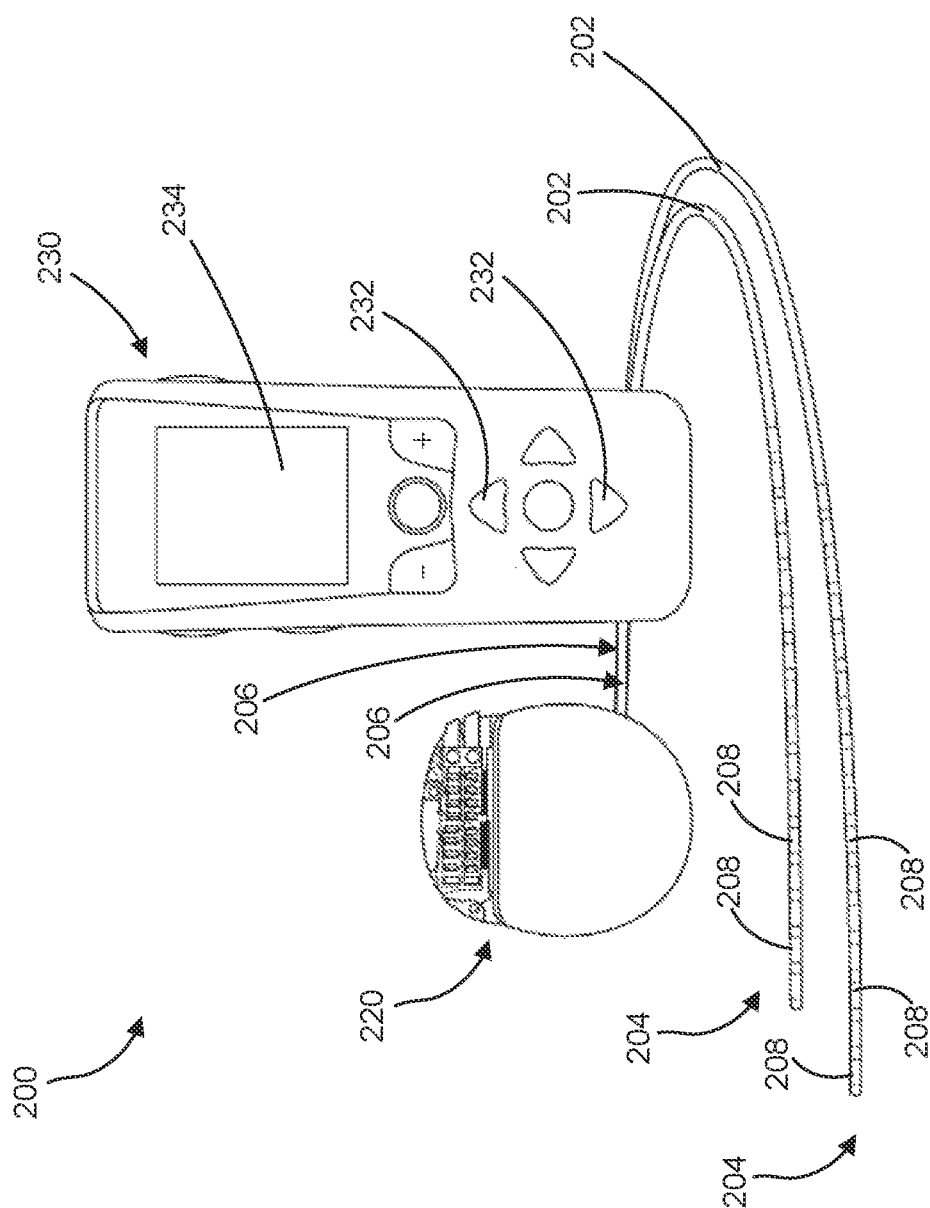
FIG. 2 illustrates an example of a kit for treating asthma using spinal cord stimulation.

FIG. 2 illustrates a kit 200 for treating asthma using spinal cord stimulation. The kit 200 includes at least one lead 202 connected to a pulse generator 220. In the illustrated example, the kit 200 includes a pair of percutaneous leads that are connected to the pulse generator 220. As will be described in more detail, the pulse generator 220 is programmed to generate electrical signals for transmission through the at least one lead 202 and for release by at least one of the contacts 208 of the lead in a predetermined location of an epidural space to mitigate asthma symptoms. In addition to treating asthma, the kit 200 can also be used to perform spinal cord stimulation to mitigate pain in the back, abdomen, chest, and other areas of the body.

In some examples, the at least one lead 202 is a temporary percutaneous lead that is implanted during a temporary trial. Alternatively, the at least one lead 202 can be a permanent lead implanted after completion of a successful temporary trial. In such alternative examples, the at least one lead 202 can be a permanent percutaneous lead or a permanent paddle lead.

Each of the at least one lead 202 has a body that extends between a distal end 204 and a proximal end 206. The body has a tubular shape of a uniform diameter and circumference that allows the at least one lead 202 to easily slide in and out through the epidural needle 110. The distal end 204 of the at least one lead 202 is configured for placement in the predetermined location of the epidural space to release electrical signals for mitigating asthma symptoms and/or treating chronic pain. The proximal end 206 is configured to connect to the pulse generator 220.

Each of the at least one lead 202 includes one or more contacts 208 positioned toward the distal end 204. Each contact 208 is configured to receive electrical signals from the pulse generator 220 and to release the electrical signals for interaction with one or more nerves in the predetermined location of the epidural space to mitigate asthma symptoms. In some examples, the contacts 208 are evenly spaced apart. The number of contacts 208 included on each of the at least one lead 202 may vary. For example, the at least one lead 202 may include at least one contact, or may include a plurality of contacts ranging anywhere from 5 to 20 contacts, or more than 20 contacts. In one example, each of the at least one lead 202 has 16 contacts.

In some examples, the proximal end 206 of each of the at least one lead 202 is configured to extend outside of the patient P's body for connection to the pulse generator 220. In such examples, the pulse generator 220 is an external device that is carried or worn by the patient P such as during a temporary trial for spinal cord stimulation.

Alternatively, the pulse generator 220 can be an implantable pulse generator that is permanently implanted under a skin surface of the patient P. In such examples, the proximal end 206 of each of the at least one lead 202 remains inside the patient P's body.

The kit 200 can further include a remote control 230 that wirelessly communicates with the pulse generator 220 to adjust the electrical signals generated from the pulse generator 220 and that are released by the one or more contacts 208. As shown in FIG. 2, the remote control 230 includes one or more input buttons 232 and a display screen 234.

As an illustrative example, the one or more input buttons 232 are selectable by the patient P to increase the frequency and/or strength of the electrical signals. For example, the one or more input buttons 232 are selectable to provide stronger asthma or pain relief. Additionally, the one or more input buttons 232 are selectable by the patient P to decrease the frequency and/or strength of the electrical signals to provide less asthma or pain relief. The one or more input buttons 232 are also selectable to alter a pulse amplitude, a pulse width, and a pulse frequency from the pulse generator 220 to optimize the electrical signals for mitigating asthma symptoms.

Figure 3:
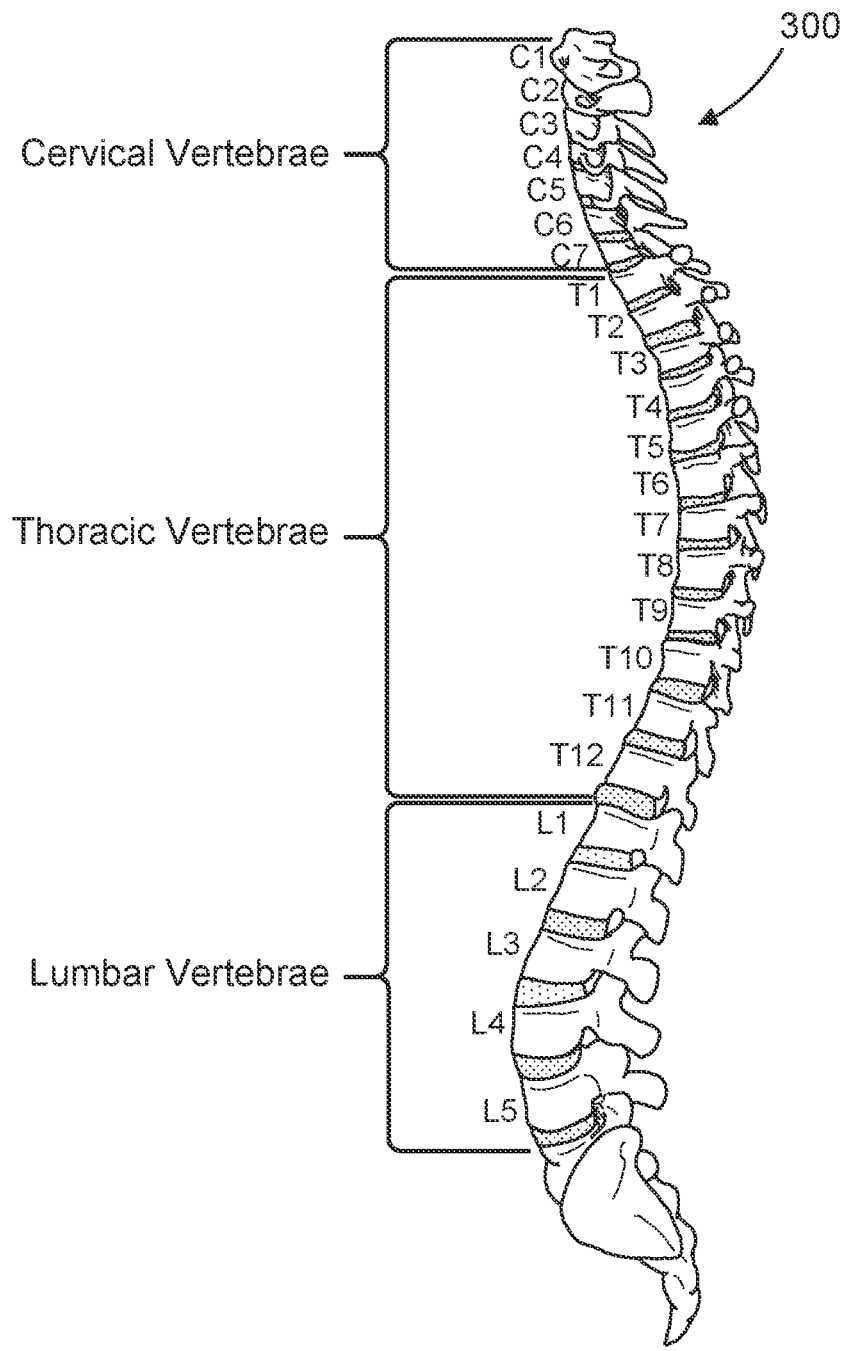
FIG. 3 illustrates an anatomical diagram of a human spine.

FIG. 3 illustrates a diagram of a spinal column 300. As shown in FIG. 3, the spinal column 300 includes cervical vertebrae C1-C7, thoracic vertebrae T1-T12, and lumbar vertebrae L1-L5. The cervical vertebrae C1-C7 are the vertebrae of the neck, immediately below the skull. The thoracic vertebrae T1-T12 lie caudal (i.e., toward the tail) of cervical vertebrae, and compose the middle segment of the spinal column 300. The lumbar vertebrae L1-L5 are bones that make up the lower back of the spinal column 300, and are above the pelvis.

Figure 4:
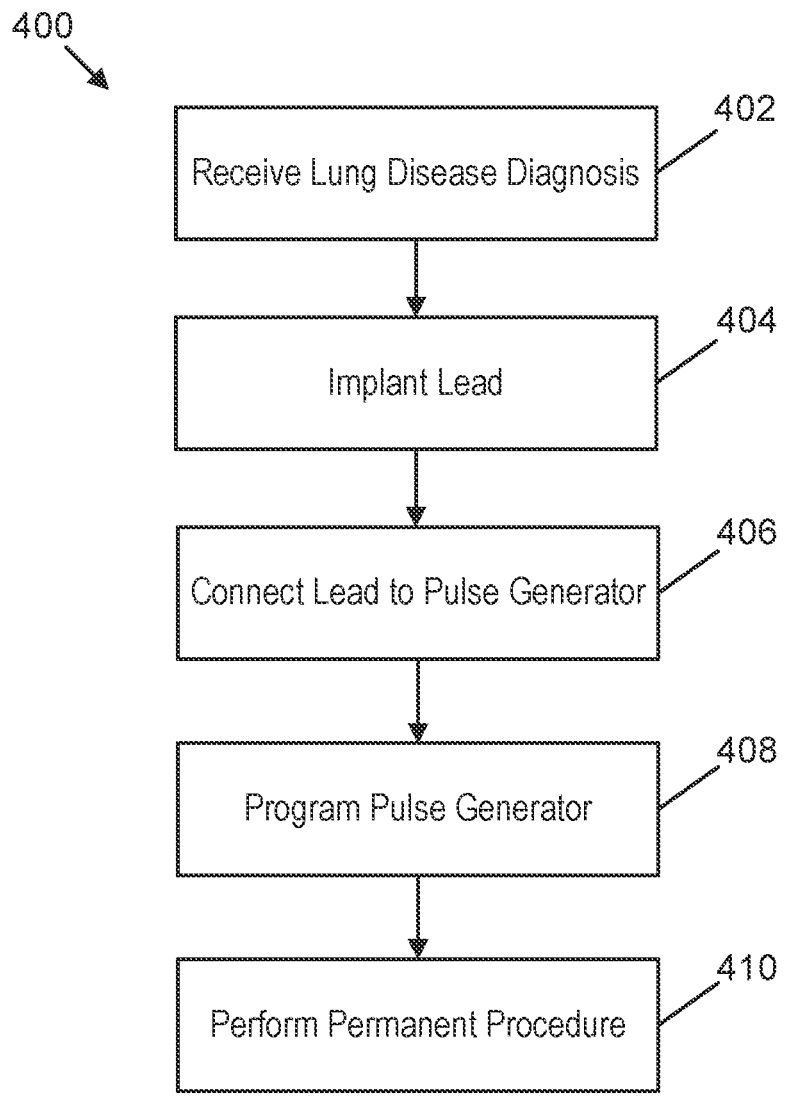
FIG. 4 illustrates an example of a method of treating lung disease symptoms using spinal cord stimulation.

FIG. 4 illustrates a method 400 of treating lung disease symptoms using spinal cord stimulation. For example, the method 400 can be performed to mitigate symptoms such as shortness of breath, difficulty breathing, wheezing, coughing, tightness of the chest, and the like. In addition to treating lung disease symptoms, the method 400 can also be performed to mitigate pain in the back, abdomen, chest, and other areas of the body using spinal cord stimulation.

As shown in FIG. 4, the method 400 can include an initial step 402 of receiving a lung disease diagnosis. For example, the lung disease diagnosis can be for asthma, chronic obstructive pulmonary disease (COPD), and/or other similar types of lung diseases. The lung disease diagnosis can be received from a pulmonologist or other qualified medical professional.

Next, the method 400 includes a step 404 of implanting the at least one lead 202, a step 406 of connecting the at least one lead 202 to the pulse generator 220, and a step 408 of programming the pulse generator 220 to generate electrical signals for mitigating symptoms of the lung disease diagnosis. The order of steps 404-408 illustrated in the example of FIG. 4 may vary. For example, the step 408 of programming the pulse generator 220 can be performed before the step 404 of implanting the at least one lead 202.

The step 404 of implanting the at least one lead 202 includes positioning the at least one contact 208 adjacent to spinal nerve tissue of the spinal cord in the predetermined location of the epidural space. In some examples, the predetermined location of the epidural space is between C7 to T5 vertebrae. In some examples, the predetermined location of the epidural space is between T1 to T5 vertebrae. In yet some further examples, the predetermined location of the epidural space is between T1 to T4 vertebrae. In yet some further examples, the predetermined location of the epidural space is between T2 to T5 vertebrae. These locations allow the electrical signals released from the at least one contact 208 to stimulate the posterior part of the thoracic spinal cord to help mitigate asthma symptoms and simultaneously relieve chest pain.

In addition to dorsal spinal column stimulation, the electrical signals released from the at least one contact 208 can also be used to stimulate the dorsal root ganglion between the T1 to T5 vertebrae to help mitigate asthma symptoms and simultaneously relieve chest pain.

By stimulating the dorsal spinal cord and/or the dorsal root ganglion between the T1-T5 vertebrae with electrical signals from the at least one contact 208, sympathetic pathways involving the chest, heart, and lungs are stimulated. The bronchial smooth muscles are controlled by sympathetically mediated beta fibers which are relaxed by the stimulation from the at least one contact 208 of the lead. The relaxation of the bronchial smooth muscles can relieve symptoms of an asthma attack. In addition to treating asthma, implanting the at least one contact 208 in the epidural space between the T1-T5 vertebrae can also mitigate pain in the chest.

In certain examples, additional contacts of the at least one lead 202 are positioned in additional locations of the epidural space to provide further pain relief. For example, step 404 can further include positioning additional contacts of the at least one lead 202 in the epidural space between the T5 and T6 vertebrae to stimulate the abdomen, and thereby provide abdomen pain relief. In some examples, the contacts of the at least one lead 202 are positioned between the T4 and T6 vertebrae to treat asthma, and reduce pain in both the chest and abdomen.

As another example, step 404 can further include positioning additional contacts of the at least one lead 202 between the T7 and T8 vertebrae, between the T8 and T9 vertebrae, between the T9 and T10 vertebrae, between the T11 and T12 vertebrae, or between the T12 and L1 vertebrae to provide lower back pain relief, in addition to positioning the at least one contact 208 between the C7 to T5 vertebrae to stimulate the chest and provide asthma relief.

Step 404 can be performed by inserting the epidural needle 110 into the predetermined location of the epidural space, and then threading the at least one lead 202 through the epidural needle 110 to position the at least one contact 208 in the predetermined location. For example, the epidural needle 110 can be inserted between C7 and T1 vertebrae, between T1 and T2 vertebrae, between T2 and T3 vertebrae, between T3 and T4 vertebrae, or between T4 and T5 vertebrae to implant the at least one contact 208 anywhere between the C7 to T5 vertebrae.

The at least one lead 202 can be inserted into the patient's body antegrade (i.e., in a superior or upward direction) or retrograde (i.e., an inferior or downward direction). Depending on how the at least one lead 202 is inserted into the epidural space (i.e., antegrade vs. retrograde), affects how the spinal cord and dorsal root ganglion are stimulated by the contacts of the lead.

In some examples, the at least one lead 202 is inserted into the patient's body retrograde (i.e., in an inferior or downward direction) to better position the at least one contact 208 next to the dorsal root ganglion. For example, the at least one lead 202 can be inserted into the epidural space starting from the C7 vertebrae and can be pushed downwardly toward the T5 vertebrae. As the at least one lead 202 is inserted retrograde, the at least one lead 202 can naturally feed out a nerve root sleeve in a posterior direction, where a dorsal root ganglion is located, such that the at least one contact 208 is positioned next to the dorsal root ganglion. This allows stimulation of the sensory portion of any given nerve root between the T1 to T5 vertebrae. Thus, the at least one contact 208 can be used to stimulate the posterior portion of somatic nerves which come off the spinal cord, to help mitigate asthma symptoms and relieve chest pain.

In step 406, the proximal end 206 of the at least one lead 202 can extend outside of the patient P's body for connection to the pulse generator 220 such as when the pulse generator is an external trial stimulator. Alternatively, the proximal end 206 of the at least one lead 202 can remain inside the patient P's body when connected to the pulse generator 220 such as in examples where the pulse generator 220 is an implantable pulse generator.

In step 408, the pulse generator 220 can be programmed to continuously generate the electrical signals to mitigate the asthma symptoms over prolonged periods of time without requiring any input from the patient P. Alternatively, the pulse generator 220 can be programmed to be controlled by the remote control 230 to generate the electrical signals on demand to mitigate symptoms upon a sudden onset of the symptoms such as during an asthma attack.

In certain examples, steps 404-408 are performed as part of a trial procedure to determine the effectiveness of treating the patient P's asthma symptoms with spinal cord stimulation. After completion of the temporary trial and upon a determination that spinal cord stimulation has effectively mitigated the patient P's asthma symptoms, the method 400 can further include a step 410 of performing a permanent spinal cord stimulation procedure.

For example, step 410 can include replacing the at least one lead 202 with a permanent lead implanted to have at least one contact positioned in the predetermined location of the epidural space (e.g., between the C7 to T5 vertebrae), connecting the permanent lead to an implantable pulse generator, and permanently implanting the implantable pulse generator under a skin surface. In the permanent spinal cord stimulation procedure, the permanent lead can be a permanent percutaneous lead or a permanent paddle lead.

Figure 5:
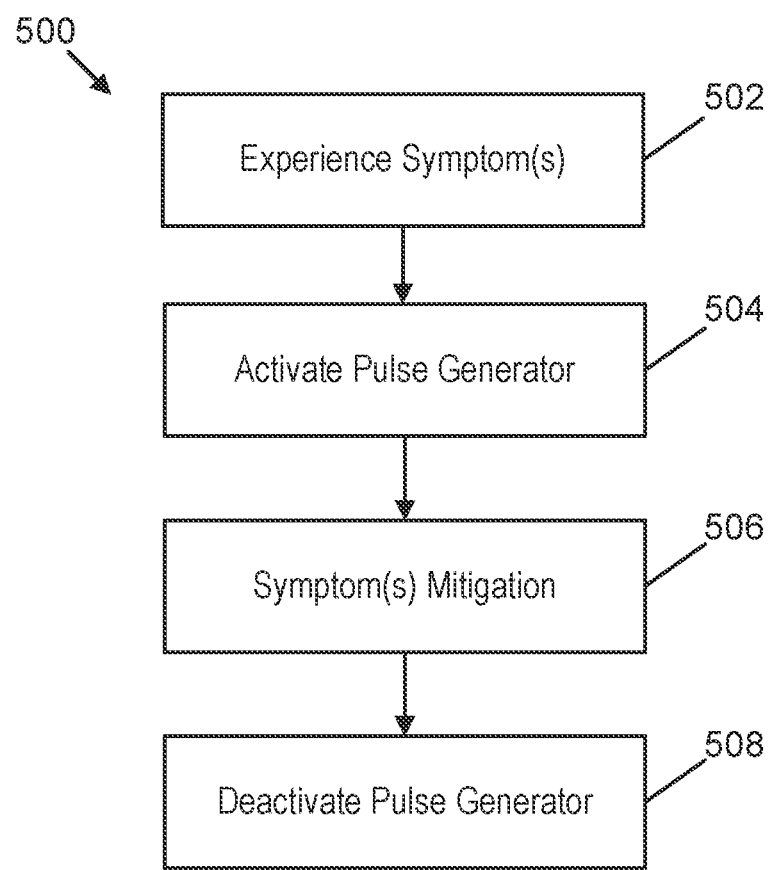
FIG. 5 illustrates another example of a method of mitigating lung disease symptoms using spinal cord stimulation.

FIG. 5 illustrates an example of a method 500 of mitigating lung disease symptoms using spinal cord stimulation. The method 500 can include a step 502 of a patient experiencing one or more symptoms such as shortness of breath, difficulty breathing, wheezing, coughing, tightness of the chest, and the like. Such symptoms may be due to a lung disease such as asthma, chronic obstructive pulmonary disease (COPD), and/or other similar types of lung diseases.

Next, the method 500 includes a step 504 of activating the pulse generator 220. For example, the patient can use the remote control 230 (see FIG. 2) to activate the pulse generator 220. The remote control 230 wirelessly communicates with the pulse generator 220 to adjust the electrical signals generated by the pulse generator 220 and released by the one or more contacts 208. In some examples, step 504 includes selecting a specific treatment protocol for mitigating lung disease symptoms using the one or more input buttons 232 and the display screen 234. For example, a treatment protocol for mitigating asthma symptoms can be selected using the one or more input buttons 232 and the display screen 234. As another example, a treatment protocol for mitigating chronic obstructive pulmonary disease (COPD) symptoms can be selected using the one or more input buttons 232 and the display screen 234. These lung disease treatment protocols can be selected separately or in addition to other treatment protocols for mitigating pain.

As another example, step 504 can include selecting the one or more input buttons 232 to increase a frequency and/or a strength of the electrical signals to provide stronger mitigation of lung disease symptoms. Additionally, step 504 can include selecting the one or more input buttons 232 to decrease the frequency and/or the strength of the electrical signals.

Next, the method 500 can include a step 506 of the patient experiencing mitigation of the one or more symptoms that were initially experienced in step 502. For example, the patient can begin to feel improved breathing such that the patient no longer has shortness of breath, difficulty breathing, wheezing, coughing, tightness of the chest, and the like.

Next, the method 500 includes a step 508 of deactivating the pulse generator 220. For example, the patient can use the remote control 230 to deactivate the pulse generator 220 after they experience mitigation of the lung disease symptoms. Advantageously, the method 500 can be performed to provide a minimum effective dosage for mitigation lung disease symptoms.

The various embodiments described above are provided by way of illustration only and should not be construed to be limiting in any way. Various modifications can be made to the embodiments described above without departing from the true spirit and scope of the disclosure.

What is claimed is:

1. A method of treating asthma, comprising:
    implanting at least one lead based on an asthma diagnosis, wherein the at least one lead is implanted to have at least one contact positioned in a predetermined location of an epidural space, wherein the predetermined location is a posterior portion of the epidural space to provide dorsal spinal column and dorsal root ganglion stimulation between C7 to T5 vertebrae;
    connecting the at least one lead to a pulse generator;
    programming the pulse generator to generate electrical signals for release by the at least one contact in the predetermined location to mitigate asthma symptoms; and
    providing a remote control having one or more input buttons, the one or more input buttons being selectable to emit a first control signal causing the pulse generator to activate a treatment protocol for mitigating the asthma symptoms, and the one or more input buttons being selectable to emit a second control signal to deactivate the treatment protocol.

2. The method of claim 1, wherein the predetermined location is between T1 to T5 vertebrae.

3. The method of claim 1, further comprising:
    inserting an epidural needle into the predetermined location; and
    threading the at least one lead through the epidural needle to position the at least one contact in the predetermined location.

4. The method of claim 3, wherein inserting the epidural needle includes inserting the epidural needle between C7 and T1 vertebrae, between T1 and T2 vertebrae, between T2 and T3 vertebrae, between T3 and T4 vertebrae, or between T4 and T5 vertebrae.

5. The method of claim 1, further comprising:
    replacing the at least one lead with a permanent lead such that the permanent lead has at least one contact positioned within the predetermined location of the epidural space;
    connecting the permanent lead to an implantable pulse generator; and
    implanting the implantable pulse generator under a skin surface.

* * * * *